(12) United States Patent
Guo et al.

(10) Patent No.: US 11,833,298 B2
(45) Date of Patent: Dec. 5, 2023

(54) FACE MASK, VENTILATION THERAPY DEVICE SYSTEM AND METHOD EXECUTED BY VENTILATION THERAPY DEVICE SYSTEM

(71) Applicant: BMC MEDICAL CO., LTD., Beijing (CN)

(72) Inventors: Qiang Guo, Beijing (CN); Zhi Zhuang, Beijing (CN)

(73) Assignee: BMC MEDICAL CO., LTD, Beijing (CN)

( * ) Notice: Subject to any disclaimer, the term of this patent is extended or adjusted under 35 U.S.C. 154(b) by 839 days.

(21) Appl. No.: 16/956,016

(22) PCT Filed: Dec. 19, 2018

(86) PCT No.: PCT/CN2018/122061
§ 371 (c)(1),
(2) Date: Jun. 19, 2020

(87) PCT Pub. No.: WO2019/120220
PCT Pub. Date: Jun. 27, 2019

(65) Prior Publication Data
US 2020/0316328 A1 Oct. 8, 2020

(30) Foreign Application Priority Data
Dec. 21, 2017 (CN) .......................... 201711395356.X (51) Int. Cl.
*A61M 16/00* (2006.01)
*A61M 16/06* (2006.01)
*G06F 3/01* (2006.01)

(52) U.S. Cl.
CPC .... *A61M 16/0003* (2014.02); *A61M 16/0633* (2014.02); *G06F 3/013* (2013.01); *A61M 2205/507* (2013.01); *A61M 2205/70* (2013.01)

(58) Field of Classification Search
CPC .......... A61M 16/0003; A61M 16/0633; A61M 2205/507; A61M 2205/70; G06F 3/013
See application file for complete search history.

(56) References Cited

U.S. PATENT DOCUMENTS

| | | | | |
|---|---|---|---|---|
| 7,575,005 B2 * | 8/2009 | Mumford | .......... | A61M 16/0633 128/205.23 |
| 2004/0163648 A1 * | 8/2004 | Burton | .............. | A61M 16/0694 128/204.21 |

(Continued)

FOREIGN PATENT DOCUMENTS

| | | |
|---|---|---|
| CN | 101618247 B | 5/2012 |
| CN | 106362259 A | 2/2017 |

(Continued)

*Primary Examiner* — Steven O Douglas
(74) *Attorney, Agent, or Firm* — Volpe Koenig (57) ABSTRACT

An embodiment of the present invention provides a mask, ventilation therapy equipment and a method executed based on the ventilation therapy equipment, and belongs to the field of ventilation therapy equipment. The mask comprises a mask body, acquisition units and output units, wherein the acquisition units are arranged on the mask body and are used for acquiring eye movement data of the eyes of a user; the eye movement data comprises action data of the eyes of the user; and the output units are connected with the acquisition units, and are used for outputting the eye movement data. By the mask, a ventilation therapy equipment system and the method executed based on the ventilation therapy equipment system, the operation intention expressed by the user with the eyes can be recognized so as to carry out follow-up control on the ventilation therapy equipment, and the user experience is greatly enhanced.

17 Claims, 10 Drawing Sheets

(56) References Cited

U.S. PATENT DOCUMENTS

2012/0249797 A1    10/2012  Haddick et al.
2013/0275139 A1    10/2013  Coleman
2016/0262608 A1     9/2016  Krueger
2018/0126107 A1*    5/2018  Valster ................ A61B 5/4836

FOREIGN PATENT DOCUMENTS

| CN | 107390863 A   | 11/2017 |
|----|---------------|---------|
| CN | 108245748 A   | 7/2018  |
| CN | 107247511 B   | 7/2019  |
| CN | 105792732 B   | 4/2020  |
| WO | 2005/094667 A2 | 10/2005 |
| WO | 2005107589 A1 | 11/2005 |
| WO | 2012/085741 A1 | 6/2012 |
| WO | 2016/053119 A1 | 4/2016 |
| WO | 2016142933 A1 | 9/2016  |
| WO | 2019120220 A1 | 6/2019  |

* cited by examiner

```
Cancel      17/10/11 21:45
Pressure            10hPa
Delay boosting      10min
```

Fig. 5B

```
Cancel      17/10/11 21:45
Pressure            10hPa
Delay boosting      10min
Shift up  ----- Shift down
```

Fig. 5C

```
            17/10/11 21:45
Pressure            10hPa
Delay boosting      10min
Confirm             Change
```

Fig. 5D

```
Cancel      3    Humidifying
            1    Expiration
                 decompression
Confirm     5    Delay boosting
```

Fig. 5E

| Cancel | ▲ 3 | Delay shutdown |
|---|---|---|
|  | 1 | Date |
| Confirm | 5 ▼ | Time |

Fig. 5F

| Cancel | ▲ 3 | Service time |
|---|---|---|
|  | 1 | About equipment |
| Confirm | 5 ▼ |  |

FACE MASK, VENTILATION THERAPY DEVICE SYSTEM AND METHOD EXECUTED BY VENTILATION THERAPY DEVICE SYSTEM

CROSS REFERENCE TO RELATED APPLICATIONS

This application is a 35 USC § 371 national stage of PCT/CN2018/122061, which was filed Dec. 19, 2018, claims priority to Chinese Application No. 201711395356.X, filed on Dec. 21, 2017, and is entitled "FACE MASK, VENTILATION THERAPY DEVICE SYSTEM AND METHOD EXECUTED BY VENTILATION THERAPY DEVICE SYSTEM," both of which are incorporated herein by reference as if fully set forth.

FIELD OF THE INVENTION

The present invention relates to ventilation therapy equipment, in particular to a mask, a ventilation therapy equipment system and a method executed based on the ventilation therapy equipment system.

BACKGROUND OF THE INVENTION

A cornea can reflect light falling on its surface. The cornea protrudes from the surface of an eyeball, so that when the eyeball moves, the light is irradiated to the cornea at a variable angle to obtain reflected light in different directions. Parallel light is irradiated to the eyeball of a person, and the light reflected by the cornea enters a camera, so that the movement track of a reflected light spot is shot, and the movement track is an eye movement track, namely a basic principle of an eye movement technology.

Traditional ventilation therapy equipment is operated through buttons, when a user sleeps or does not want to do too many actions to operate the ventilation therapy equipment, or the ventilation therapy equipment is far away from the body or in other circumstances (such as disabled people without hands), the ventilation therapy equipment is inconveniently controlled by hands directly, the defects of the traditional button operation are obvious.

SUMMARY OF THE INVENTION

An embodiment of the present invention aims to provide a mask, a ventilation therapy equipment system and a method executed based on the ventilation therapy equipment system, the mask, the ventilation therapy equipment system and the method executed based on the ventilation therapy equipment system can detect the operation intention expressed by a user with eyes so as to carry out follow-up control on ventilation therapy equipment, so that the user experience is greatly enhanced.

In order to achieve the above object, the embodiment of the present invention provides a mask comprising: a mask body, acquisition units and output units, wherein the acquisition units are arranged on the mask body and are used for acquiring eye movement data of eyes of the user, and the eye movement data comprises action data of the eyes of the user; and the output units are connected with the acquisition units and are used for outputting the eye movement data. The eye movement data of the eyes of the user can be acquired by the acquisition units, so that the operation intention expressed by the user with the eyes can be detected, the user can issue a control instruction through the eyes, and the user experience is greatly enhanced.

Preferably, the mask further comprises display units arranged on the mask body. By means of the cooperation of the display units, it is possible to detect more complex intentions expressed by the user with the eyes in order to subsequently perform the operation desired by the user more accurately.

Preferably, the mask body comprises a forehead support on which the acquisition units are mounted. When the user wears the mask, the acquisition units are more favorable for acquiring eye movement data of the user.

Preferably, the mask body comprises a forehead support on which the display units are mounted. When the user wears the mask, the user can look directly at the display units more conveniently.

Preferably, the mask body further comprises a forehead pad located in the middle of the forehead support and used for being in contact with the forehead of the user. When the user wears the mask, the user feels more comfortable, and the mask is firmer to wear.

Preferably, the mask body further comprises a display unit support connected to the lower portion of the forehead support and capable of fixing the acquisition units at positions where the acquisition units can acquire the eye movement data of the user more favorably, and fixing the display units at positions where the user can look directly at the display units more conveniently.

Preferably, the display units are embedded in the display unit support and are respectively positioned on the middle of the left side of the display unit support and the middle of the right side of the display unit support. When the user wears the mask, the display units respectively correspond to the left eye and the right eye of the user, so that the user can look directly at the display units more conveniently.

Preferably, the acquisition units are mounted on the display unit support and are respectively positioned at the upper left corner and the upper right corner of the inner side of the display unit support. When the user wears the mask, the acquisition units can acquire data in multiple directions, and the eye movement data of the user can be acquired more favorably.

Preferably, the mask body further comprises a nose mask and a rubber pad, the nose mask is in contact with the face of the user via the rubber pad. When the user wears the mask, the user feels more comfortable, and the mask is firmer to wear.

Preferably, the mask body further comprises forehead head-mounted supports which are positioned on two sides of the forehead support, so that the user can wear the mask more conveniently.

Preferably, the mask body further comprises nose mask head-mounted supports which are positioned on two sides of the nose mask, so that the user can wear the mask more conveniently.

The present invention also provides a ventilation therapy equipment system which comprises the mask described above and ventilation therapy equipment, wherein the ventilation therapy equipment comprises a processor connected to the output units of the mask and used for adjusting the running of the ventilation therapy equipment according to the eye movement data. The eye movement data of the eyes of the user can be acquired by the acquisition units in the mask, so that the operation intention expressed by the user with the eyes is conveniently detected to control the ventilation therapy equipment, the running of the ventilation therapy equipment can be controlled by the user through the eyes, and the user experience is greatly enhanced.

Preferably, when the mask comprises the display units, the processor is further used for: controlling the display units to display to-be-executed operation information of the ventilation therapy equipment; determining the positions, at which the user looks directly with eyes, of the display units according to the eye movement data; and adjusting the running of the ventilation therapy equipment according to the to-be-executed operation information displayed at the positions, at which the user looks directly with eyes, of the display units. Through the cooperation of the display units, more complex intentions expressed by the user with the eyes can be detected, so that the running of the ventilation therapy equipment can be adjusted more accurately, and the operation desired by the user can be completed.

Preferably, the processor is further used for: recording eye movement calibration data when the user looks directly at a plurality of fixed positions of the display units with eyes; and calibrating the determined positions, at which the user looks directly with eyes, of the display units according to the eye movement calibration data. After calibration, the determined positions, at which the user looks directly with eyes, of the display units can be more accurate.

Preferably, the processor is further used for: controlling the ventilation therapy equipment to enter a sleep mode when the eye movement data cannot be detected in a first period of time; and/or controlling the ventilation therapy equipment to enter a wake-up mode when the eye movement data indicates that the user blinks eyes for a preset number of times in a second period of time. When the user does not use the ventilation therapy equipment for a long time, the ventilation therapy equipment can enter the sleep mode for saving energy, and when the user needs to use the ventilation therapy equipment, the ventilation therapy equipment can be waken up at any time, so that normal use of the ventilation therapy equipment is not affected.

An embodiment of the present invention also provides a method executed based on the ventilation therapy equipment system, the method comprising the following steps: acquiring the eye movement data of the eyes of the user, wherein the eye movement data comprises action data of the eyes of the user; and adjusting the running of the ventilation therapy equipment according to the eye movement data. The eye movement data of the eyes of the user are acquired, so that the operation intention expressed by the user with the eyes is conveniently detected to control the ventilation therapy equipment, the running of the ventilation therapy equipment can be controlled by the user through the eyes, and the user experience is greatly enhanced.

Preferably, when the ventilation therapy equipment system comprises the display units, the method further comprises the step of controlling the display units to display the to-be-executed operation information of the ventilation therapy equipment. The display units can inform the user of an operation executable by the ventilation therapy equipment for selection by the user.

Preferably, the step of adjusting the running of the ventilation therapy equipment system according to the eye movement data comprises: determining the positions, at which the user looks directly with eyes, of the display units according to the eye movement data; and adjusting the running of the ventilation therapy equipment according to the to-be-executed operation information displayed at the positions, at which the user looks directly with eyes, of the display units. Through the cooperation of the display units, more complex intentions expressed by the user with the eyes can be detected, so that the running of the ventilation therapy equipment can be adjusted more accurately, and the operation desired by the user can be completed.

Preferably, before controlling the display units to display the to-be-executed operation information of the ventilation therapy equipment system, the method further comprises: recording eye movement calibration data when the user looks directly at a plurality of fixed positions of the display units with eyes. The standard data generated when the user looks directly at certain positions of the display units can be obtained through the recorded eye movement calibration data, so that the determined positions, at which the user looks directly, of the display units can be subsequently calibrated.

Preferably, before adjusting the running of the ventilation therapy equipment according to the to-be-executed operation information displayed at the positions, at which the user looks directly with eyes, of the display units, the method further comprises: calibrating the determined positions, at which the user looks directly with eyes, of the display units according to the eye movement calibration data. After calibration, the determined positions, at which the user looks directly, of the display units can be more accurate.

Preferably, the method further comprises: controlling the ventilation therapy equipment to enter a sleep mode when the eye movement data cannot be detected in a first period of time; and/or controlling the ventilation therapy equipment to enter a wake-up mode when the eye movement data indicates that the user blinks eyes for a preset number of times in a second period of time. When the user does not use the ventilation therapy equipment for a long time, the ventilation therapy equipment can enter the sleep mode for saving energy, and when the user needs to use the ventilation therapy equipment, the ventilation therapy equipment can be waken up at any time, so that normal use of the ventilation therapy equipment is not affected.

According to the above technical solution, the invention provides the mask, the ventilation therapy equipment system and the method executed based on the ventilation therapy equipment system, wherein the method comprises the steps of acquiring the eye movement data of the eyes of the user, wherein the eye movement data comprises action data of the eyes of the user; and adjusting the running of the ventilation therapy equipment according to the eye movement data. The operation intention expressed by the user with the eyes can be detected so as to carry out follow-up control on the ventilation therapy equipment, and the user experience is greatly enhanced.

Additional features and advantages of the embodiments of the present invention will be described in detail in the detailed description which follows.

BRIEF DESCRIPTION OF DRAWINGS

The accompanying drawings, which are comprised to provide a further understanding of embodiments of the present invention and are incorporated in and constitute a part of the specification, illustrate the embodiments of the present invention together with the detailed description below, serve to explain, but not limit the embodiments of the invention. In the drawings.

Description of Reference Numerals

| | |
|---|---|
| 1, 5-acquisition unit | 2, 4-output unit |
| 3-cable plug | 6-forehead pad |
| 7-wiring groove | 8-cross beam |
| 9-forehead support | 10-nose mask |
| 11-nose mask pad | 12-ventilation pipeline |
| 13-cable | 14-ventilation therapy equipment |
| 15-socket | 16-ventilation pipeline connector |
| 17, 18-display unit | 19, 20-power line and data line of display unit |
| 21-display unit support | 22, 23-forehead head-mounted support |
| 24, 25-nose mask head-mounted support | 26-mask body |

DETAILED DESCRIPTION OF THE EMBODIMENTS

The detailed description of the embodiments of the present invention will be described in conjunction with the accompanying drawings, and it shall be understood that the detailed description described here are only for describing and explaining the embodiments of the present invention and not to limit the embodiments of the present invention.

Figure 1:
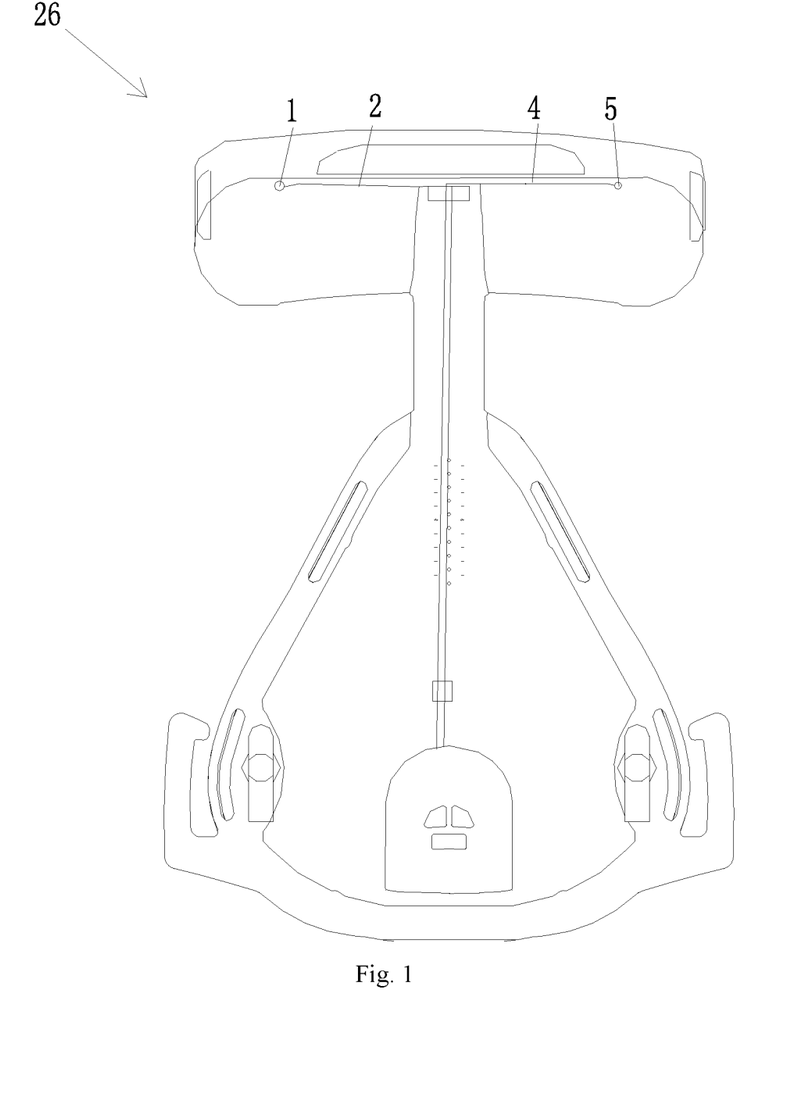
FIG. 1 is a structural schematic diagram of a mask provided by one embodiment of the present invention.

FIG. 1 is a structural schematic diagram of a mask provided by one embodiment of the present invention. As shown in FIG. 1, the mask comprises: a mask body 26, acquisition units 1 and 5 and output units 2 and 4, wherein the acquisition units 1 and 5 are arranged on the mask body and are used for acquiring eye movement data of eyes of a user, and the eye movement data comprises action data of the eyes of the user; and the output units 2 and 4 are connected with the acquisition units 1 and 5 and used for outputting the eye movement data.

The acquisition units 1 and 5 can be infrared acquisition units, such as infrared cameras, or other equipment having an acquisition function, the number of the acquisition units is two preferably, and the acquisition units are respectively a left eye acquisition unit and a right eye acquisition unit and are used for acquiring eye movement data of the left eye and eye movement data of the right eye. Illumination units can be embedded in acquisition units 1 and 5 for providing full field-of-view illumination. In addition, the mask can further comprise the output units 2 and 4, such as data lines and wireless output modules.

The eye movement data can comprise action data of the eyes of the user, and actions comprise, for example, blinking, eye closure, eye movement (gaze, eye movement and follow-up) and the like. The acquisition units 1 and 5 can acquire the eye movement data of the eyes of the user, such as different reflected light of different actions of the eyes, since the light of the illumination units is reflected in different ways when the eyes move. The output units 2 and 4 can be used for outputting the eye movement data.

Figure 2A:
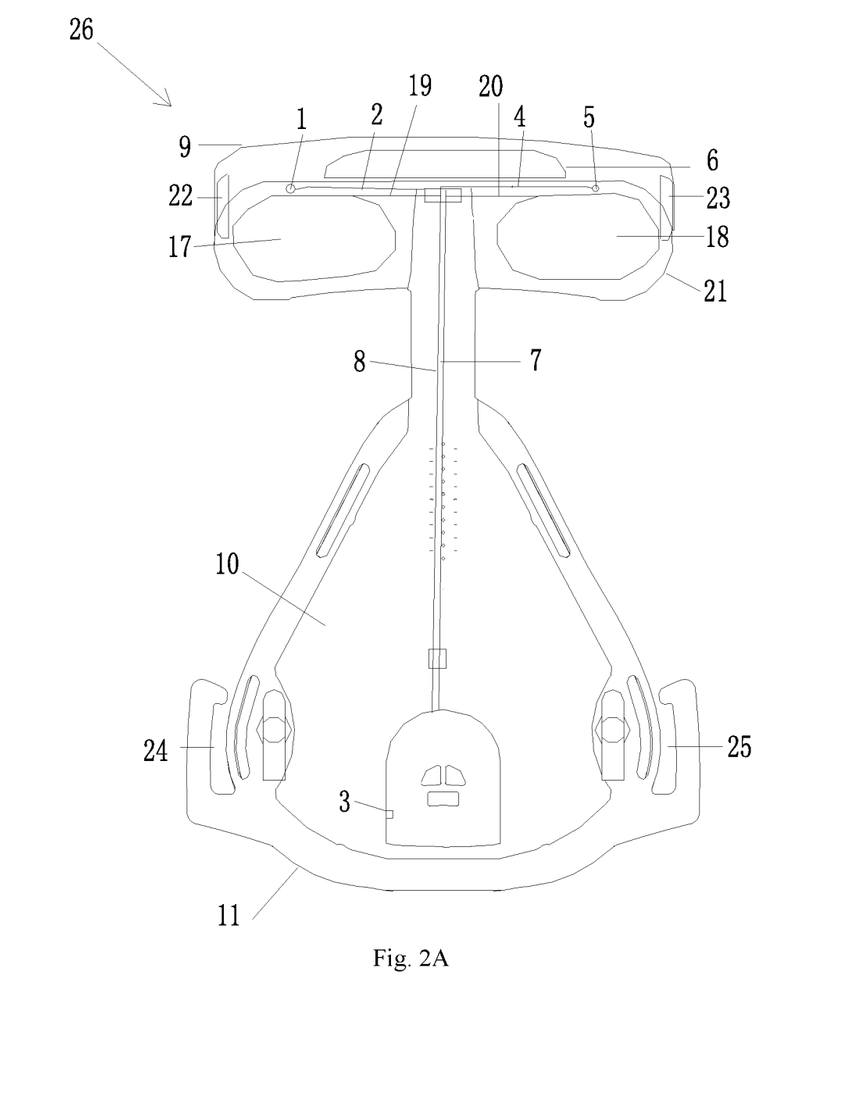
FIG. 2A is a front view of a mask provided by another embodiment of the present invention.
Figure 2B:
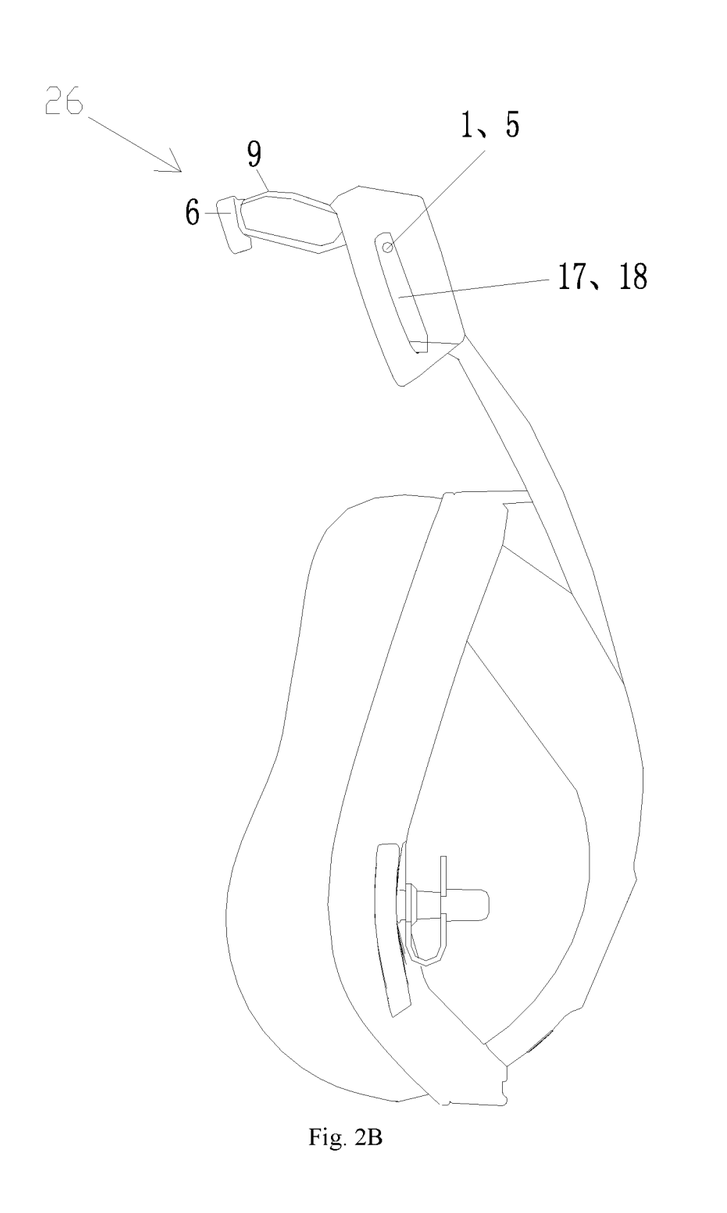
FIG. 2B is a side view of the mask provided by another embodiment of the present invention.

FIG. 2A is a front view of a mask provided by another embodiment of the present invention; FIG. 2B is a side view of a mask provided by another embodiment of the present invention. As shown in FIGS. 2A-2B, in order that the user can use the eyes to express more complex intentions, the display units 17 and 18, such as display screens, can further be arranged on the mask body 26, and can comprise a right eye display unit and a left eye display unit.

In addition, the mask can further comprise a cable plug 3, a forehead pad 6, a wiring groove 7, a cross beam 8, a forehead support 9, a nose mask 10, a rubber pad 11, a display unit support 21, forehead head-mounted supports 22 and 23 and nose mask head-mounted supports 24 and 25, the specific structures are as follows: the forehead pad 6 is positioned in the middle of the forehead support 9 and is used for being in contact with the forehead of the user, thus, when wearing the mask, the user feels more comfortable, and the mask is firmer to wear; the display unit support 21 is connected to the lower portion of the forehead support 9, can fix the acquisition units at positions where the acquisition units can acquire the eye movement data of the user more favorably, and can fix the display units at the positions where the user can look directly at the display units more conveniently; the display units 17 and 18 are embedded in the display unit support 21 and are respectively positioned in the middle of the left side of the display unit support 21 and the middle of the right side of the display unit support 21, when the user wears the mask, the display units correspond to the left eye and the right eye of the user respectively, and thus, the user can look directly at the display units more conveniently; the acquisition units 1 and 5 are mounted on the display unit support 21, and are respectively positioned at the upper left corner and the upper right corner of the inner side of the display unit support 21, when the user wears the mask, the acquisition units can acquire data in multiple directions, and the eye movement data of the user can be acquired more favorably; the nose mask 10 is in reliable contact with the face of the user via the rubber pad 11, when the user wears the mask, the user feels more comfortable, and the mask is firmer to wear; the output units 2 and 4 and data lines and power lines 19 and 20 of the display units are gathered to the cable plug 3 through the wiring groove 7 in the display unit support 21 and the mask cross beam 8; the forehead head-mounted supports 22 and 23 are positioned on two sides of the forehead support 9, the nose mask head-mounted support 24 and 25 are positioned on two sides of the nose mask 10, and thus, the user can wear the mask more conveniently.

Figure 3A:
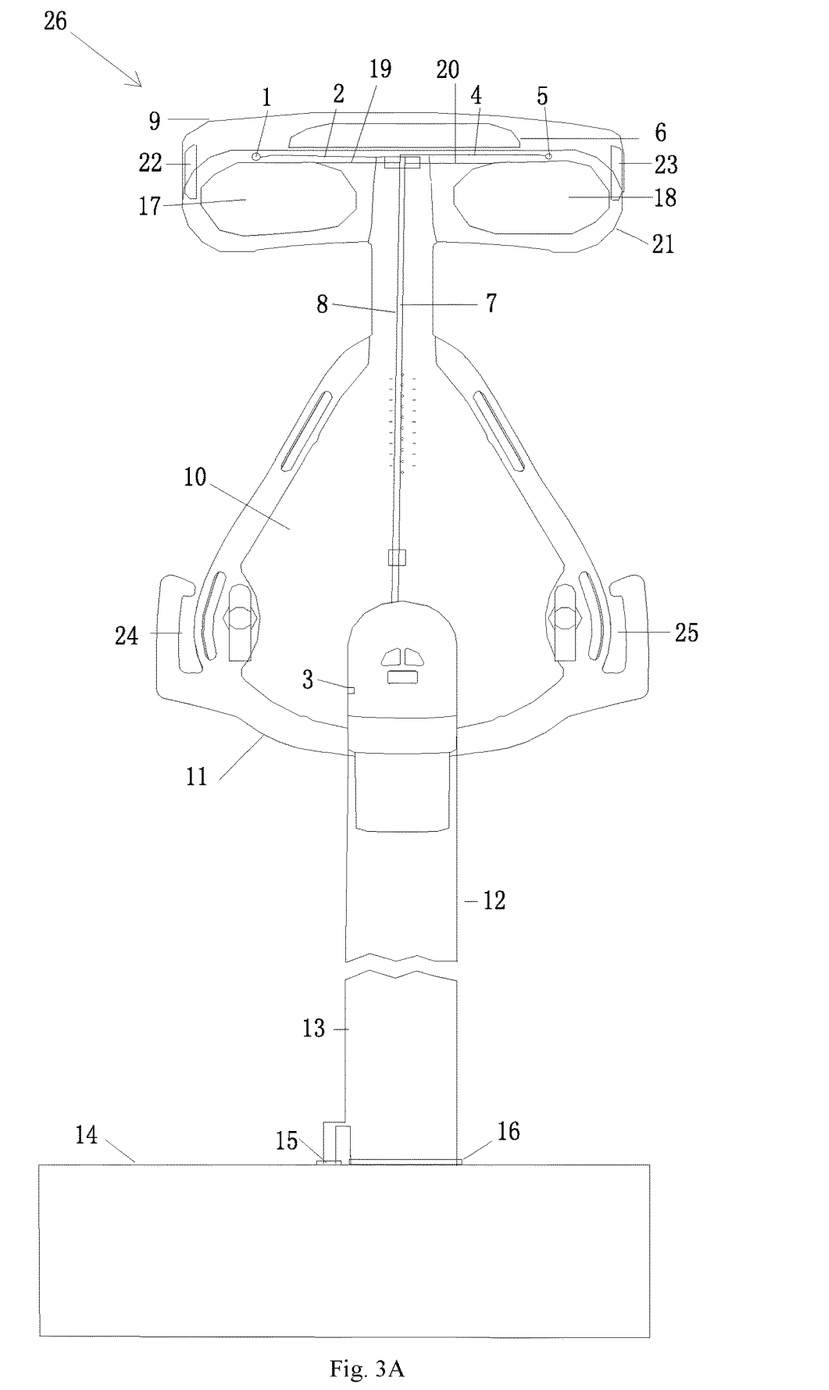
FIG. 3A is a front view of a ventilation therapy equipment system provided by one embodiment of the present invention.
Figure 3B:
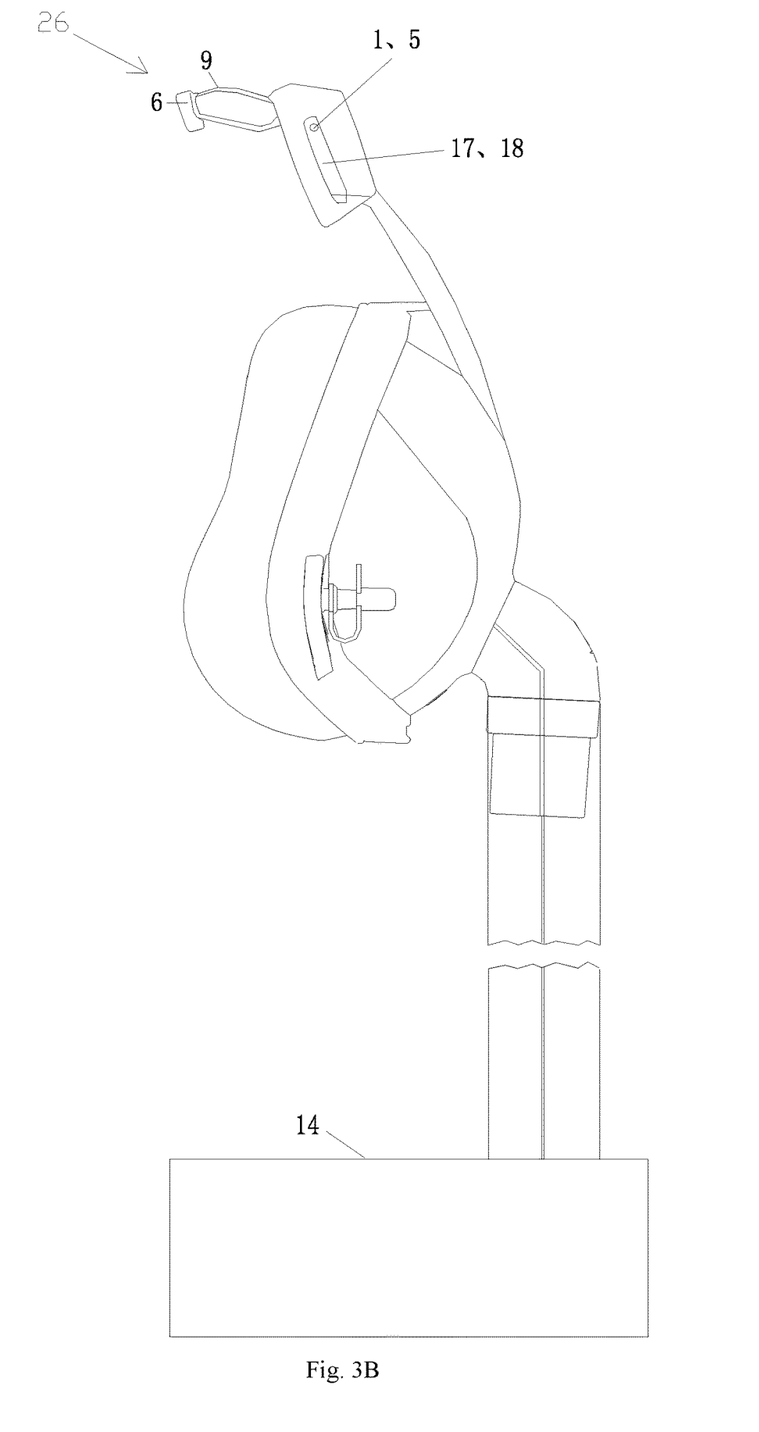
FIG. 3B is a side view of a ventilation therapy equipment system provided by another embodiment of the present invention.

FIG. 3A is a front view of a ventilation therapy equipment system provided by one embodiment of the present invention; FIG. 3B is a side view of a ventilation therapy equipment system provided by another embodiment of the present invention. As shown in FIGS. 3A-3B, the ventilation therapy equipment system comprises the mask described above, and further comprises a ventilation pipeline 12, a cable 13, ventilation therapy equipment 14, a socket 15 and a ventilation pipeline connector 16. The specific structures are as follows: a pipeline portion is used for connecting the mask with the ventilation therapy equipment 14 and comprises the cable 13 and the ventilation pipeline 12, one end of the cable 13 is provided with a female socket, the other end of the cable 13 is provided with a plug, the female socket is connected with the cable plug 3, and the plug is connected with the socket 15 of the ventilation therapy equipment 14; and the ventilation pipeline 12 is used for connecting the nose mask 10 with the ventilation pipeline connector 16 of the ventilation therapy equipment 14.

In addition, the ventilation therapy equipment 14 can also comprise a processor (not shown) for adjusting the running of the ventilation therapy equipment according to the eye movement data. The ventilation therapy equipment 14 can be preset with rules such as user eye closure, blinking, eye movement to the left several times and movement to the right several times for different operational adjustments. The following description is based on a sleep mode and a wake-up mode when the ventilation therapy equipment 14 is in operation:

when no eye movement data (user eye closure) is detected within a first period of time (for example, 1 minute), the processor can control the ventilation therapy equipment 14 to enter the sleep mode in which the brightness of illumination sources in the acquisition units 1 and 5 can be weakened, the display units 17 and 18 are switched off or the brightness of the display units 17 and 18 is weakened, but the acquisition units 1 and 5 still keep acquiring the eye movement data so as to be convenient for the user to wake up the ventilation therapy equipment 14. In addition, in the present invention, the condition for triggering the ventilation therapy equipment 14 to enter the sleep mode is not limited to the no detection of the eye movement data, but can also be other actions performed by the eyes of the user according to a preset rule.

When the eye movement data indicates that the user blinks eyes for a preset number of times (for example, five times) within a second period of time (for example, within four seconds) (or when the eyes of the user perform other actions according to a preset rule), the processor controls the ventilation therapy equipment 14 to be waken up, restore the brightness of the illumination sources in the acquisition units 1 and 5, switch on the display units 17 and 18 or restore the brightness of the display units 17 and 18, and the ventilation therapy equipment 14 is brought into the wake-up mode for normal operation. In addition, in the present invention, the condition for triggering the ventilation therapy equipment 14 to enter the wake-up mode is not limited to blinking for a preset number of times in the second period of time, but can also be other actions performed by the eyes of the user according to a preset rule.

When the eyeballs of the user move to the left several times within a third period of time (for example, three times, or perform other actions, depending on a preset rule), the ventilation therapy equipment 14 shifts down; and when the eyeballs of the user move to the right several times within the third period of time (for example, three times, or perform other actions, depending on the preset rule), the ventilation therapy equipment 14 shifts up.

When the mask comprises the display units 17 and 18, the processor is further used for: controlling the display units 17 and 18 to display to-be-executed operation information of the ventilation therapy equipment; and determining the positions, at which the user looks directly with eyes, of the display units 17 and 18 according to the eye movement data. When the user looks at different positions of the display units 17 and 18 with eyeballs, the positions of the reflected light are also different. The acquisition units 1 and 5 can acquire the positions of the light reflected by the eyeballs, and the processor can determine the positions, at which the user looks directly with eyes, of the display units 17 and 18, so that follow-up operations can be carried out in conjunction with the content displayed by the display units 17 and 18.

Figure 4A:
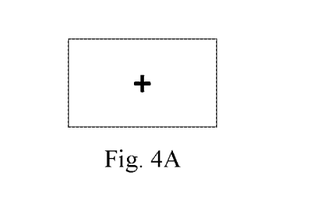
FIGS. 4A-4E are schematic diagrams of a display unit provided by one embodiment of the present invention.
Figure 4B:
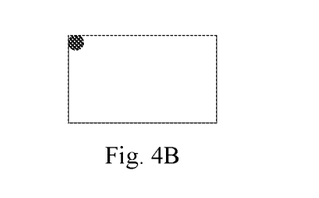
Figure 4C:
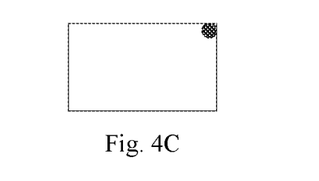
Figure 4D:
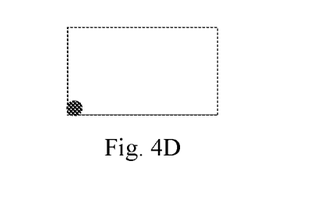
Figure 4E:
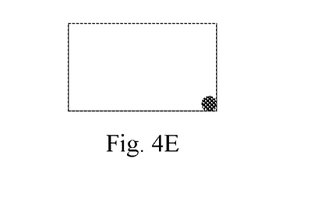

In order to make the determination of the positions, at which the user looks directly, of the display units 17 and 18 accurate, the processor can also record eye movement calibration data when the user looks directly at a plurality of fixed positions of the display units 17 and 18 with eyes; the ventilation therapy equipment 14 also comprises a memory for storing the eye movement calibration data. The processor is further used for calibrating the determined positions, at which the user looks directly with eyes, of the display units 17 and 18 according to the eye movement calibration data. The specific method is as follows:

FIGS. 4A-4E are schematic diagrams of a display unit 103 provided by one embodiment of the present invention. As shown in FIGS. 4A-4E, a starting-up interface is displayed by the display units 17 and 18, and the brightness of the display units 17 and 18 is adjust to a relatively proper position according to the light sensitivity, and the user wears the mask. '+' as shown in FIG. 4A can occur in the middles of the display units 17 and 18, the user looks directly at '+' in the middles of the display units 17 and 18 with eyes, and the light irradiates on the eyeballs of the user, the acquisition units 1 and 5 acquire the light reflected from corneas, and reflected light spots are photographed, and after the user looks directly at '+' stably for more than a period of time (for example, 3 seconds), the memory records the coordinates of the positions where the light spots are located, and the coordinates of the positions where the light spots are located correspond to the positions of '+' in the middles of the display units 17 and 18; then, four round spots can appear in the upper left corner, the upper right corner, the lower left corner and the lower right corner of each of the display units 17 and 18, as shown in FIGS. 4B-4E, the user looks directly at the four round spots respectively with eyes, and after light reflected by the corneas is photographed by the acquisition units 1 and 5, the coordinates of the positions where the light spots are located are recorded by the memory, and respectively correspond to the four round spots at the four corners of the display units 17 and 18.

After the above-mentioned learning, if the processor finds that the acquisition units 1 and 5 acquire the coordinates of the positions where the same light spots are located, it is possible to determine the positions, at which the user looks directly with eyes, of the display units 17 and 18 at the moment, in this way, the determined positions, at which the user looks directly with eyes, of the display units 17 and 18 are quite accurate, and the determined positions, at which the user looks directly with eyes, of the display units 17 and 18 in above embodiment can be calibrated.

In addition, after learning as described above, the processor can also determine the positions, at which the user looks directly with eyes, of the display units 17 and 18 according to the eye movement calibration data and the eye movement data directly.

FIGS. 5A-5G are schematic diagrams of a display unit during adjustment of the ventilation therapy equipment system according to another embodiment of the present invention. As shown in FIGS. 5A-5G, the processor is used for adjusting the running of the ventilation therapy equipment 14 according to the to-be-executed operation information displayed at the positions, at which the user looks directly with eyes, of the display units 17 and 18. The working mode of the ventilation therapy equipment 14 in the wake-up mode according to one embodiment of the present invention is described in detail below:

1) Start of Therapy

Figure 5A:
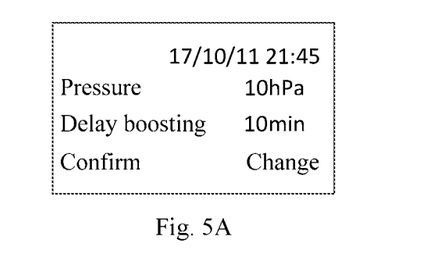
FIGS. 5A-5G are schematic diagrams of a display unit during adjustment of the ventilation therapy equipment system provided by another embodiment of the present invention.
Figure 5B:
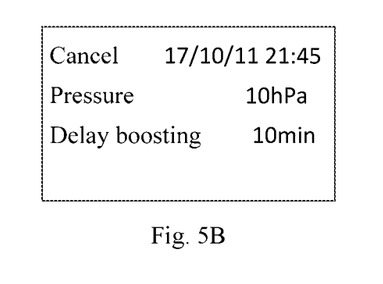

After the ventilation therapy equipment 14 is switched on, images first presented on the display units 17 and 18 are shown in FIG. 5A, the user looks at 'confirm' at the lower left corner, the ventilation therapy equipment 14 begins to ventilate, and the display interfaces of the display units 17 and 18 are shown in FIG. 5B.

2) Adjustment of Gears of a Humidifier

Figure 5C:
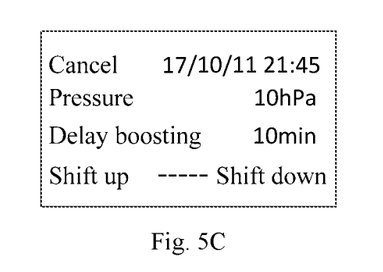

If the user uses the humidifier, humidification gears can be adjusted during ventilation, and the display interfaces of the display units 17 and 18 are shown in FIG. 5C: the bottom row is used for adjusting the humidification gears, the left is up, the right is down, and the middle '-' indicates the current gear. If the user looks at 'up', the ventilation therapy equipment 14 shifts up, if the user looks at 'down', the ventilation therapy equipment 14 shifts down, and the middle '-' will vary along with adjustment by the user. The highest gear of the humidifier is the fifth gear, the middle displays the current gear, and if the current gear is fifth gear, five are all turned on; and when the are all turned off, it shows that the humidifier is switched off.

3) Stopping of Therapy

When in a ventilation state, the user looks at 'cancel' at the upper left corners of the display units 17 and 18, and then therapy can stop.

4) Change of Parameters of the Ventilation Therapy Equipment

Figure 5D:
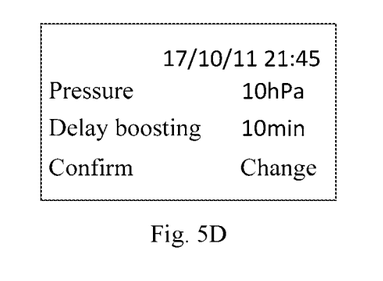

The ventilation therapy equipment 14 is started to enter a start-up interface as shown in FIG. 5D. The user looks at 'change' at the lower right corner to enter a user parameter setup interface, as shown in FIG. 5E.

The number preceding the name of an option is the value currently set for the option. If the user needs to change the set value, the to-be-changed option needs to be activated at first, the user looks at the option needing to be changed, and the option and the value thereof are shaded. If the user wants to increase data, the user looks at '▲' for a period of time (for example, more than 2 seconds), and then the data can be increased; and if the user wants to decrease the data, the user looks at '▼'. After completing setting, the user looks at 'confirm', and after activation of the changed option is canceled and shadow disappears, then change of the parameters is finished.

Figure 5E:
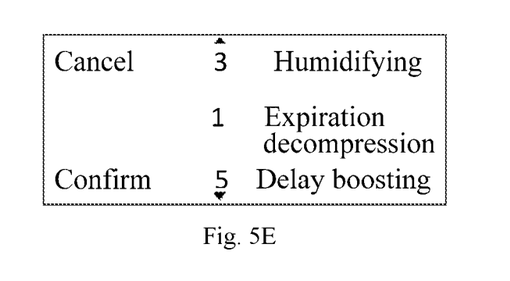
Figure 5F:
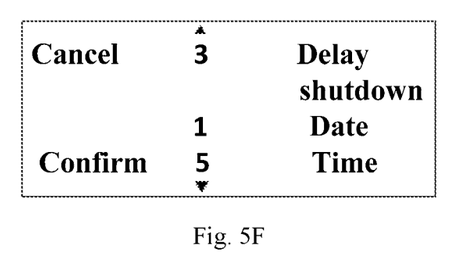
Figure 5G:
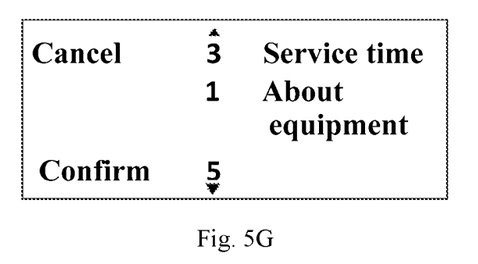

The options which the user of the ventilation therapy equipment 14 can view and change are in three pages, and besides content shown in FIG. 5E, the other options are as shown in FIGS. 5F-5G.

5) Page Turning

Since more than one page is operable by the user, the user also needs to turn pages. After change of the information of the page is confirmed, no activated options exist. If a patient needs to turn up, the line of sight of the patient moves up from the lowermost edge '▼' in the middle to '▲', the patient looks at '▲', and the displayed content is turned up. If the patient needs to turn down, the operation is reversed, the line of sight of the patient moves down from the uppermost edge '▲' in the middle to '▼', and the patient looks at '▲'.

6) Exit of Change

After change of the user is finished, the user can look at 'cancel' to enter exit of change of the parameters.

The description of the different parameters can be shown in Table 1 below.

TABLE 1 parameter description of ventilation therapy equipment

| Names of setting options | Setting range | Description |
| --- | --- | --- |
| Humidifier | Off, 1-5 | The humidifier totally has five gears, and along with increasing of set values, temperature and humidity are continuously increased. '0' shows closing of a humidifying function. During delivery, the default of the option is '2' |
| Expiration decompression | Off, 1-3 | During expiration of the user, a therapy machine can decompress automatically to increase the comfort level of the user. Decompression is divided into three gears, and along with increasing of the set values, decompression is continuously increased during expiration. 'Off' shows closing of the function. During delivering, the default setting of the option is 'closing' |
| Delay boosting | 0-longest boosting delay | In order to make the user feel comfortable and fall asleep easily, gas pressure generated by the ventilation therapy equipment 14 is increased step by step from small to large after starting, the time interval of rising from initial pressure to therapy pressure can be adjusted, and numerical value stepping is 1 minute. During delivery, the default of the option is '10 minutes'. The display units 17 and 18 can display the countdown remaining time of delay boosting, and minute is taken as a unit |
| Delay shutdown | On, off | After therapy stops under the condition that the humidifier works, the equipment still keeps working for about 15 minutes at quite low pressure (about 3 hPa) so as to blow away residual moisture in the humidifier to prevent accumulated water from damaging the equipment. If the setting is set as '0', the function of delay shutdown is closed, and at the moment, if therapy stops, the ventilation therapy equipment 14 will stop outputting immediately. During delivery, the default setting of the option is '0', namely, the function is closed |
| Date | 2000 Jan. 1-2099 Dec. 31 | Date setting, the setting can correct the internal date of the equipment |
| Time | 00:00-23:59 | Time setting, the setting can correct internal clock of the equipment |
| Service time | 0-50000 hours | Service time displays the duration of service of the ventilation therapy equipment 14 by the user. The service time can be eliminated |
| About equipment | — | The related information of the ventilation therapy equipment is displayed, the option only can be checked by the user, and cannot be corrected. Model: the model of the ventilation therapy equipment; SN: the serial number of the ventilation therapy equipment; firmware version: software version of the ventilation therapy equipment; ID: information of a graph library, language and the like. |

Figure 6:
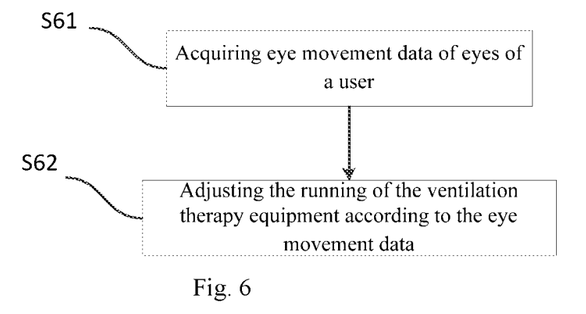
FIG. 6 is a flow chart of a method executed based on a ventilation therapy equipment system provided by one embodiment of the present invention.

FIG. 6 is a flow chart of a method executed based on a ventilation therapy equipment system provided by one embodiment of the present invention. As shown in FIG. 6, the method comprises: acquiring the eye movement data of eyes of the user, wherein the eye movement data comprises action data of the eyes of the user (step S61); and adjusting the running of the ventilation therapy equipment according to the eye movement data (step S62).

Figure 7:
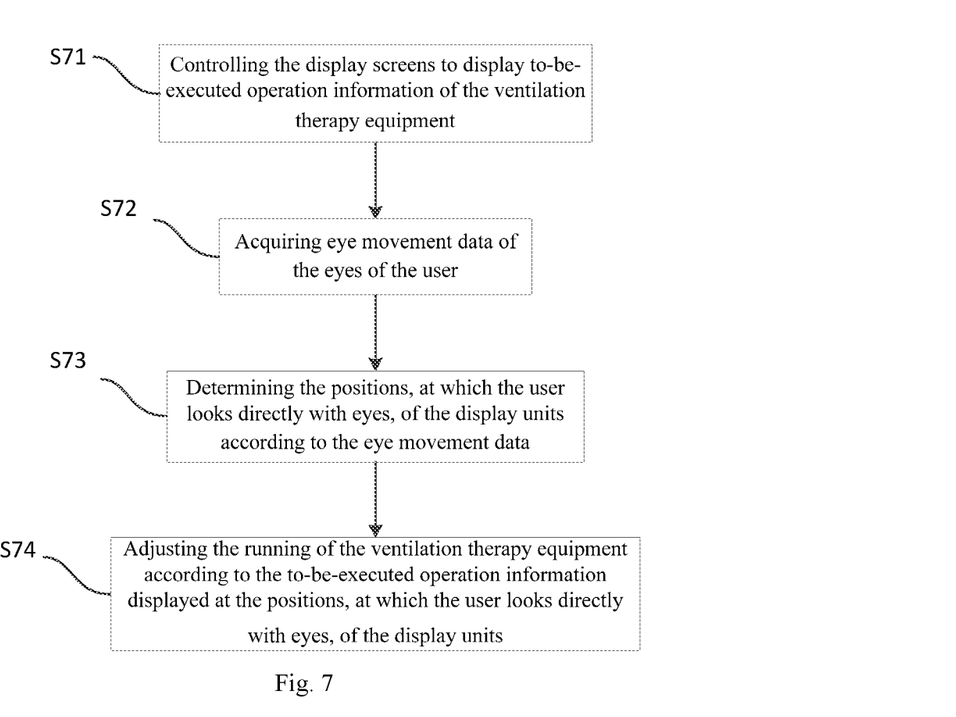
FIG. 7 is a flow chart of a method executed based on a ventilation therapy equipment system provided by another embodiment of the present invention.

FIG. 7 is a flow chart of a method executed based on a ventilation therapy equipment system provided by another embodiment of the present invention. As shown in FIG. 7, the method comprises: controlling the display units to display to-be-executed operation information of the ventilation therapy equipment (step S71); acquiring the eye movement data of the eyes of the user, wherein the eye movement data comprises movement data of the eyes of the user (step S72); determining the positions, at which the user looks directly with eyes, of the display units according to the eye movement data (step S73); and adjusting the running of the ventilation therapy equipment according to the to-be-executed operation information displayed at the positions, at which the user looks directly with eyes, of the display units (step S74).

Figure 8:
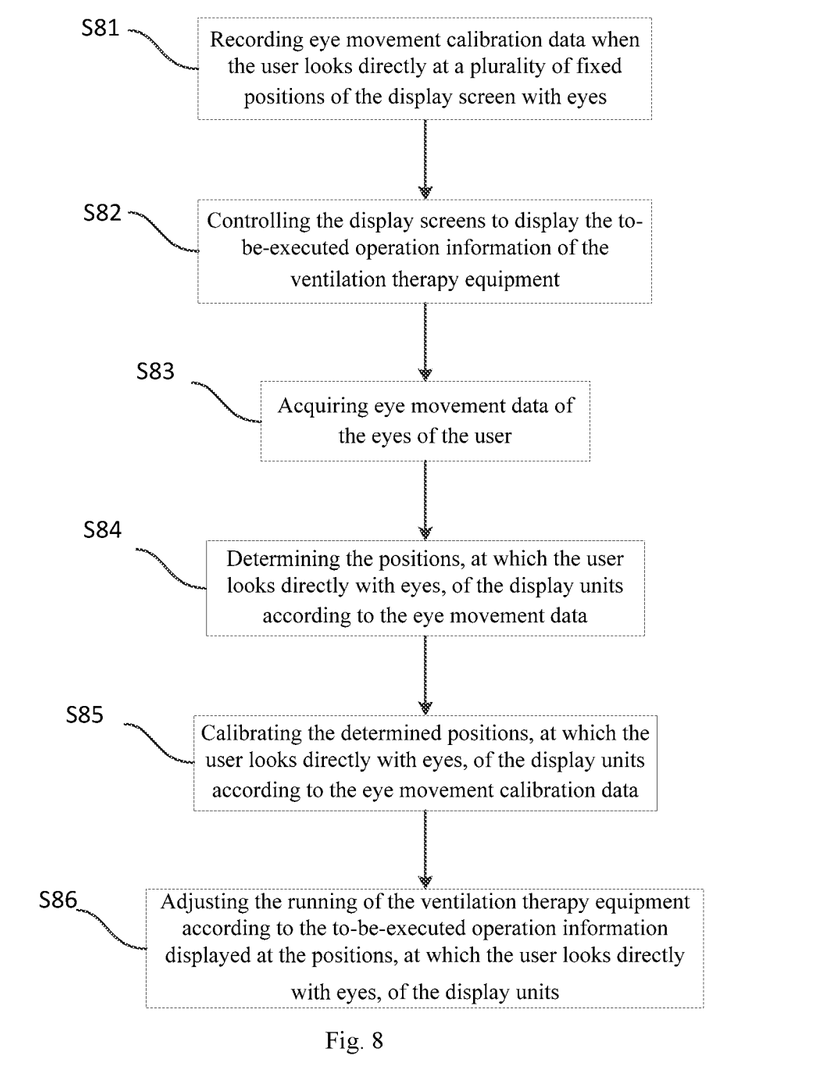
FIG. 8 is a flow chart of a method executed based on a ventilation therapy equipment system provided by another embodiment of the present invention.

FIG. 8 is a flow chart of a method executed based on a ventilation therapy equipment system provided by another embodiment of the present invention. As shown in FIG. 8, the method comprises: recoding the eye movement calibration data when the user looks directly at a plurality of fixed positions of the display units with eyes (step S81); controlling the display units to display the to-be-executed operation information of the ventilation therapy equipment (step S82); acquiring the eye movement data of the eyes of the user, wherein the eye movement data comprises movement data of the eyes of the user (step S83); determining the positions, at which the user looks directly with eyes, of the display units according to the eye movement data (step S84); calibrating the determined positions, at which the user looks directly with eyes, of the display units according to the eye movement calibration data (step S85); and adjusting the running of the ventilation therapy equipment according to the to-be-executed operation information displayed at the positions, at which the user looks directly with eyes, of the display units (step S86).

Preferably, the method further comprises: controlling the ventilation therapy equipment to enter a sleep mode when eye movement data is not detected in a first period of time.

Preferably, the method further comprises: controlling the ventilation therapy equipment to enter a wake-up mode when the eye movement data indicates that the user blinks eyes for a preset number of times in a second period of time.

Through the technical solution, by adopting the mask, the ventilation therapy equipment system and the method executed based on the ventilation therapy equipment system, the operation intention expressed by the user with eyes can be detected so as to carry out follow-up control on the ventilation therapy equipment, and the user experience is greatly enhanced.

Although an alternative embodiment of the present invention has been described in detail in conjunction with the accompanying drawings, the embodiments of the present invention are not limited to the specific details of the foregoing implementation modes, and various simple modifications of the technical solution of the embodiments of the present invention can be made within the technical concept of the embodiments of the present invention, which fall within the scope of protection of the embodiments of the present invention.

It should be further understood that specific technical features described in the foregoing implementation modes can be combined in any suitable manner without departing from the spirit or scope of the present invention. In order to avoid unnecessary repetition, various possible combinations of the embodiments of the present invention will not be described further.

Those skilled in the art will appreciate that all or part of the steps in the method of the foregoing embodiments can be implemented by associated hardware instructed by a program, and the program is stored in a storage medium, and comprises a plurality of instructions for causing a single chip microcomputer, chip, or processor to perform all or part of the steps of the methods described in the various embodiments herein. The foregoing storage medium comprises: a USB flash disk, a mobile hard disk, a read-only memory (ROM), a random access memory (RAM), a diskette or an optical disk and other various media capable of storing program codes.

In addition, any combination of the various implementation modes of the embodiments of the present invention can be made without departing from the spirit of the embodiments of the present invention, which should also be regarded as the disclosure of the embodiments of the invention.

The invention claimed is:

1. A mask, wherein the mask comprises:
   a mask body;
   acquisition units which are arranged on the mask body and are used for acquiring eye movement data of the eyes of a user, wherein the eye movement data comprises action data of the eyes of the user; and
   output units which are connected with the acquisition units and are used for outputting the eye movement data,
   wherein the mask further comprises display units arranged on the mask body.

2. The mask according to claim 1, wherein the mask body comprises a forehead support on which the acquisition units are mounted.

3. The mask according to claim 1, wherein the mask body comprises a forehead support on which the display units are mounted.

4. The mask according to claim 3, wherein the mask body further comprises a display unit support which is connected to the lower portion of the forehead support.

5. The mask according to claim 4, wherein the display units are embedded in the display unit support, and are respectively positioned in the middle of the left side of the display unit support and the middle of the right side of the display unit support.

6. The mask according to claim 4, wherein the acquisition units are mounted on the display unit support, and are respectively positioned at the upper left corner and the upper right corner of the inner side of the display unit support.

7. The mask according to claim 2, wherein the mask body further comprises a forehead pad which is positioned in the middle of the forehead support and used for being in contact with the forehead of the user.

8. The mask according to claim 1, wherein the mask body further comprises a nose mask and a rubber pad, and the nose mask is in contact with the face of the user via the rubber pad.

9. A ventilation therapy equipment system, wherein the ventilation therapy equipment system comprises:
   the mask according to claim 1; and
   ventilation therapy equipment, wherein the ventilation therapy equipment comprises a processor connected with the output units of the mask and used for adjusting the running of the ventilation therapy equipment according to the eye movement data.

10. The ventilation therapy equipment system according to claim 9, wherein the processor is further used for:
    controlling the display units to display to-be-executed operation information of the ventilation therapy equipment;
    determining positions, at which the user looks directly with eyes, of the display units according to the eye movement data; and adjusting the running of the ventilation therapy equipment according to the to-be-executed operation information displayed at the positions, at which the user looks directly with eyes, of the display units.

11. The ventilation therapy equipment system according to claim 10, wherein,
the processor is further used for:
recording eye movement calibration data when the user looks directly at a plurality of fixed positions of the display units with eyes; and
calibrating the determined positions, at which the user looks directly with eyes, of the display units according to the eye movement calibration data.

12. The ventilation therapy equipment system according to claim 9, wherein the processor is further used for:
controlling the ventilation therapy equipment to enter a sleep mode when the eye movement data cannot be detected in a first period of time; and/or
controlling the ventilation therapy equipment to enter a wake-up mode when the eye movement data indicates that the user blinks eyes for a preset number of times in a second period of time.

13. A method executed based on the ventilation therapy equipment system according to claim 9, wherein the method comprises:
controlling the display units to display to-be-executed operation information of the ventilation therapy equipment;
acquiring eye movement data of the eyes of the user, wherein the eye movement data comprises action data of the eyes of the user; and
adjusting the running of the ventilation therapy equipment according to the eye movement data.

14. The method according to claim 13, wherein after controlling the display units to display the to-be-executed operation information of the ventilation therapy equipment, the method further comprises:
determining the positions, at which the user looks directly with eyes, of the display units according to the eye movement data; and
adjusting the running of the ventilation therapy equipment according to the to-be-executed operation information displayed at the positions, at which the user looks directly with eyes, of the display units.

15. The method according to claim 14, wherein before controlling the display units to display the to-be-executed operation information of the ventilation therapy equipment system, the method further comprises:
recording eye movement calibration data when the user looks directly at a plurality of fixed positions of the display units with eyes.

16. The method according to claim 15, wherein before adjusting the running of the ventilation therapy equipment according to the to-be-executed operation information displayed at the positions, at which the user looks directly with eyes, of the display units, the method further comprises:
calibrating the determined positions, at which the user looks directly with eyes, of the display units according to the eye movement calibration data.

17. The method according to claim 13, wherein the method further comprises:
controlling the ventilation therapy equipment to enter a sleep mode when the eye movement data cannot be detected in a first period of time; and/or
controlling the ventilation therapy equipment to enter a wake-up mode when the eye movement data indicates that the user blinks eyes for a preset number of times in a second period of time.

* * * * *